United States Patent [19]

Long, Jr. et al.

[11] Patent Number: 5,697,369

[45] Date of Patent: Dec. 16, 1997

[54] METHOD AND APPARATUS FOR DISEASE, INJURY AND BODILY CONDITION SCREENING OR SENSING

[75] Inventors: David M. Long, Jr., El Cajon, Calif.; Mark L. Faupel, Conyers, Ga.

[73] Assignee: Biofield Corp., Roswell, Ga.

[21] Appl. No.: 352,504

[22] Filed: Dec. 9, 1994

Related U.S. Application Data

[63] Continuation-in-part of Ser. No. 213,021, Mar. 14, 1994, Pat. No. 5,427,098, which is a continuation-in-part of Ser. No. 859,170, Mar. 27, 1992, Pat. No. 5,320,101, which is a continuation-in-part of Ser. No. 579,970, Sep. 10, 1990, Pat. No. 5,099,844, which is a division of Ser. No. 288,572, Dec. 22, 1988, Pat. No. 4,955,383.

[51] Int. Cl.$^6$ ............................................. A61B 5/05
[52] U.S. Cl. ........................ 128/65.31; 128/639; 128/734
[58] Field of Search ......................... 128/639, 733, 128/734, 653.1, 731; 364/413.02; 382/181, 209, 217, 218; 395/10, 11, 21, 23, 924

[56] References Cited

U.S. PATENT DOCUMENTS

| | | |
|---|---|---|
| 4,094,307 | 6/1978 | Young et al. ................. 364/413.05 |
| 4,112,491 | 9/1978 | Bugay ......................... 364/413.05 |
| 4,328,809 | 5/1982 | Hirschowitz et al. . |
| 4,407,300 | 10/1983 | Davis . |
| 4,557,271 | 12/1985 | Stoller et al. . |
| 4,557,273 | 12/1985 | Stoller et al. . |
| 4,866,645 | 9/1989 | Lish ................................... 364/602 |
| 4,955,383 | 9/1990 | Faupel ............................. 128/653.1 |
| 5,099,844 | 3/1992 | Faupel ............................. 128/653.1 |
| 5,130,563 | 7/1992 | Nabet et al. ........................ 364/807 |
| 5,181,256 | 1/1993 | Kamiya . |
| 5,204,938 | 4/1993 | Skapura et al. . |
| 5,208,900 | 5/1993 | Gardner . |
| 5,311,876 | 5/1994 | Olsen et al. ........................ 128/731 |
| 5,320,101 | 6/1994 | Faupel et al. .................... 128/653.1 |
| 5,325,862 | 7/1994 | Lewis et al. ....................... 128/731 |
| 5,427,098 | 6/1995 | Faupel et al. .................... 128/653.1 |
| 5,447,166 | 9/1995 | Gevins .............................. 128/731 |

*Primary Examiner*—Brian L. Casler
*Attorney, Agent, or Firm*—Sixbey, Friedman, Leedom & Ferguson PC; Daniel W. Sixbey

[57] ABSTRACT

A method and apparatus for measuring biopotentials at a test site on a human or animal subject and determining therefrom the existence or status of a condition at such test site. The efficacy of treatment of a condition is monitored by comparing values obtained from biopotentials taken before treatment with those obtained during or after treatment. For disease diagnosis or screening, values obtained from biopotential measurements taken during a test period are processed in a neural network which has been programmed to recognize potential value patterns indicative of a disease condition.

16 Claims, 3 Drawing Sheets

METHOD AND APPARATUS FOR DISEASE, INJURY AND BODILY CONDITION SCREENING OR SENSING

This application is a continuation-in-part application of Ser. No. 08/213,021 filed Mar. 14, 1994 now U.S. Pat. No. 5,427,098, which is a continuation-in-part of Ser. No. 07/859,170 filed Mar. 27, 1992, now U.S. Pat. No. 5,320, 101, which is a continuation-in-part application of Ser. No. 07/579,970, filed Sep. 10, 1990, now U.S. Pat. No. 5,099, 844, which is a divisional application of Ser. No. 07/288,572 filed Dec. 22, 1988, now U.S. Pat. No. 4,955,383.

TECHNICAL FIELD

The present invention relates generally to a method and apparatus for screening or sensing disease states, injury sites or bodily conditions, in a living organism by detecting the DC potential of the electromagnetic field present between a reference and a plurality of test points on the living organism to measure the gradient of electrical activity which occurs as a function of biological activity.

BACKGROUND ART

In recent years the theory that measurement of the potential level of the electromagnetic field of a living organism can be used as an accurate screening and diagnostic tool is gaining greater acceptance. Many methods and devices have been developed in an attempt to implement this theory. For example, U.S. Pat. No. 4,328,809 to B. H. Hirschowitz et at. deals with a device and method for detecting the potential level of the electromagnetic field present between a reference point and a test point of a living organism. Here, a reference electrode and a test electrode provide DC signals indicative of the potential level of the electromagnetic field measured between the reference point and the test point. These signals are provided to an analog-to-digital converter which generates a digital signal as a function thereof, and a processor provides an output signal indicative of a parameter or parameters of the living organism as a function of this digital signal.

Similar biopotential measuring devices are shown by U.S. Pat. No. 4,407,300 to Davis, and U.S. Pat. No. 4,557,271 and U.S. Pat. No. 4,557,273 to Stroller et al. Davis, in particular, discloses the diagnosis of cancer by measuring the electromotive forces generated between two electrodes applied to a subject.

Often, the measurement of biopotentials has been accomplished using an electrode array, with some type of multiplexing system to switch between electrodes in the array. The aforementioned Hirschowitz et al. patent contemplates the use of a plurality of test electrodes, while U.S. Pat. No. 4,416,288 to Freeman and U.S. Pat. No. 4,486,835 to Bai disclose the use of measuring electrode arrays.

Unfortunately, previous methods for employing biopotentials measured at the surface of a living organism as a diagnostic tool, while basically valid, are predicated upon an overly simplistic hypothesis which does not provide an effective diagnosis for many disease states. Prior methods and devices which implement them operate on the basis that a disease state is indicated by a negative polarity which occurs relative to a reference voltage obtained from another site on the body of a patient, while normal or non-malignant states, in the case of cancer, are indicated by a positive polarity. Based upon this hypothesis, it follows that the detection and diagnosis of disease states can be accomplished by using one measuring electrode situated externally on or near the disease site to provide a measurement of the polarity of the signal received from the site relative to that from the reference site. Where multiple measuring electrodes have been used, their outputs have merely been summed and averaged to obtain one average signal from which a polarity determination is made. This approach can be subject to major deficiencies which lead to diagnosis inaccuracy, particularly where only surface measurements are taken.

First, the polarity of diseased tissue underlying a recording electrode has been found to change over time. This fact results in a potential change which confounds reliable diagnosis when only one external recording electrode is used. Additionally, the polarity of tissue as measured by skin surface recording is dependent not only upon the placement of the recording electrode, but also upon the placement of the reference electrode. Therefore, a measured negative polarity is not necessarily indicative of diseases such as cancer, since polarity at the disease site depends in part on the placement of the reference electrode.

When many electrodes are used to sense small DC biopotentials at the surface of the skin, such as in screening for breast cancer, it is crucial for the sensing electrodes to be accurately placed and spaced so that two adjacent electrodes are not overlapping or sensing the same test area. If these tolerances are not accurately maintained, false readings are likely to result.

As disease states such as cancer progress, they produce local effects which include changes in vascularization, water content, and cell division rate. These effects alter ionic concentrations which can be measured at the skin surface and within the neoplastic tissues. Other local effects, such as distortions in biologically closed electrical circuits, may occur. A key point to recognize is that these effects do not occur uniformly around the disease site. For example, as a tumor grows and differentiates, it may show wide variations in its vascularity, water content and cell division rate, depending on whether examination occurs at the core of the tumor (which may be necrotic) or at the margins of the tumor (which may contain the most metabolically active cells). The tumor may not respond significantly to growth factors, while the growth factors and the enzymes produced may significantly affect the normal cells surrounding the tumor. Once this fact is recognized, it follows that important electrical indications of disease are going to be seen in the relative voltages recorded from a number of sites at and near a diseased area, and not, as previously assumed, on the direction (positive vs. negative) of polarity.

The accurate measurement of DC biopotentials for sensing or screening for disease, injury or bodily functions is very difficult to accomplish, for the DC potentials to be sensed are of a very low amplitude. Due to factors such as the low DC potentials involved and the innate complexity of biological systems, the collected data signals tend to include a substantial volume of noise which makes accurate analysis difficult. Also, biological systems are notorious for their complexity, nonlinearity and nonpredictability, and wide variations from the norm are not uncommon. Thus it is necessary to develop a method and apparatus for obtaining the necessary data from the measurement of biopotentials and then to extract and analyze pertinent information which is relevant to a condition under study.

DISCLOSURE OF THE INVENTION

It is a primary object of the present invention to provide a novel and improved method and apparatus for disease, injury or bodily function screening or sensing which employs the measurement and analysis of DC biopotentials taken from the area of a site on a living organism to monitor the efficacy of a treatment for the disease, injury, or bodily function.

Another object of the present invention is to provide a novel and improved method and apparatus for condition screening or sensing wherein DC biopotentials from the area of a site on a living organism are measured and then processed in a neural network which has been taught to recognize information patterns indicative of a particular condition.

A further object of the present invention is to provide a novel and improved method and apparatus for disease, injury or bodily condition screening or sensing wherein DC biopotentials are received from a plurality of sites at and near a suspected area of disease, injury or condition change on a living organism. A maximum potential differential is then obtained from the averages of multiple biopotential values taken over time and subsequently provided to a neural network which has been taught to recognize patterns indicative of a disease, injury or other bodily condition.

Yet a further object of the present invention is to provide a novel and improved method and apparatus for disease, injury or condition screening or sensing wherein DC biopotentials are received from a plurality of measuring electrodes located on the skin of a subject in the area of a suspected disease, injury or condition change site. A maximum potential differential is then obtained from the averages of multiple biopotential values taken over time, and the averages as well as the maximum potential differential are subsequently provided to a neural network which has been taught to recognize patterns indicative of a particular condition.

Another object of the present invention is to provide a novel and improved method and apparatus for disease, injury or bodily condition screening or sensing wherein analog biopotentials are received from a plurality of measuring electrodes located on the skin of a subject in the area of the site of a suspected condition. These analog potentials are subjected to mathematical processing and the resultant analog values are then provided to an analog neural network which has been taught to recognize patterns indicative of a bodily condition.

A further object of the present invention is to provide methods and devices for reducing the impedance at an electrode-skin interface on a subject.

Another object of the present invention is to provide a biopotential sensing electrode including a gel which incorporates a chemical agent to reduce impedance at the electrode-skin interface.

A still further object of the present invention is to provide a novel and improved method and apparatus for bodily condition screening or sensing wherein a multiplicity of DC biopotentials are received from each of a plurality of measuring electrodes and a complex pattern resulting from phasicity changes in these biopotentials is analyzed by a neural network.

BEST MODE FOR CARRYING OUT THE INVENTION

Figure 1:
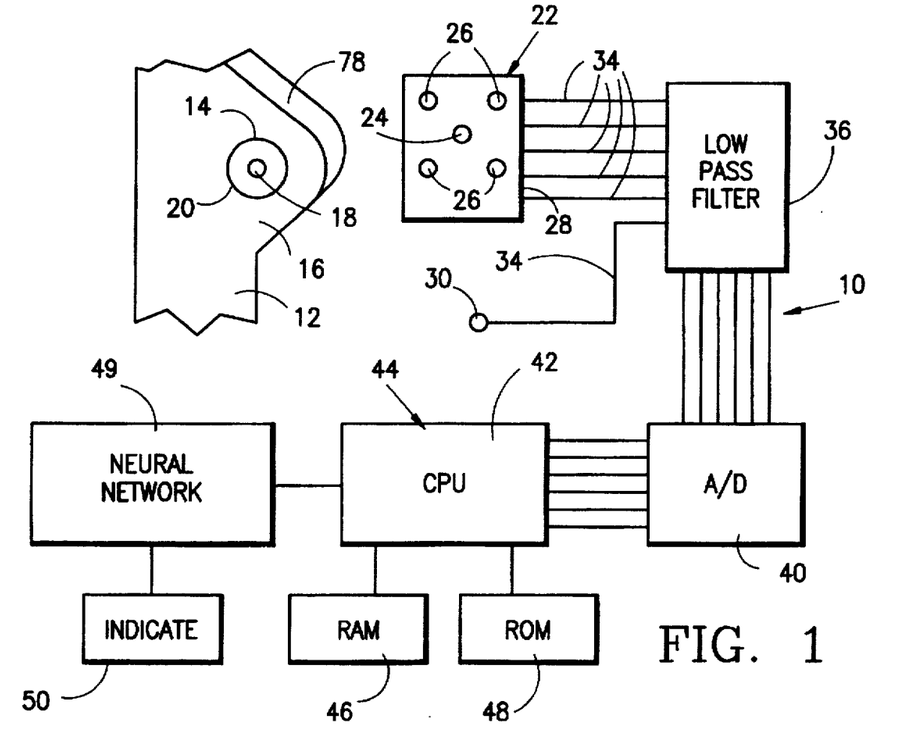
FIG. 1 is a block diagram of the apparatus of the present invention.

FIG. 1 discloses a basic block diagram of the apparatus of the present invention indicated generally at 10 for performing a discriminant analysis to obtain both raw data signals and a differential signal for a pattern recognition device that then discriminates between patterns to achieve disease, injury or other condition screening or sensing. For purposes of illustration, the apparatus 10 will be described in connection with methods involving the screening for, or diagnosing of breast cancer. However, it should be recognized that the method and apparatus of the invention can be similarly employed for screening or diagnosis at other sites involving other conditions of a living human or animal. For example, the apparatus and method to be described can be used to detect disease conditions such as infection, ischemia, spasm, arthritis or other injury, or non-disease conditions such as ovulation, labor, abnormalities of labor, and fetal distress.

In FIG. 1, a human subject 12 may have a cancerous lesion 14 on one breast 16. This cancerous lesion has a core 18 and an outer zone 20 surrounding the core where various differing local effects, such as changes in vascularization, water content and cell division rate occur. The outer zone 20 will include normal cells surrounding the lesion, for these cells often exhibit a much greater biopotential effect in response to tumor growth than does the actual tumor. Assuming first, for purposes of discussion, that the location of the lesion 14 is not known, and the device 10 is to be used to screen the breast 16 to determine whether or not a disease condition exists, skin surface potentials will be measured in an area of the breast, including the zone 20 using an electrode array 22. The device and method of this invention contemplate the use of a variety of different electrode arrays depending upon the intended application for which the device 10 is used. For example, in the diagnosis of clinically symptomatic breast or skin lesions, the electrode array should cover various areas of the lesion as well as relatively normal tissue near the lesion site. For breast cancer screening (where patients are asymptomatic) the array should give maximum coverage of the entire breast surface. The aim in both of these cases is to measure the gradient of electrical activity which occurs as a function of the underlying biological activity of the organ system. The number of electrodes used in the measurement will also be a function of specific application, and breast cancer screening may require the use of as few as twelve or as many as one hundred or more electrodes 24 for each breast.

Figures 2, 6:
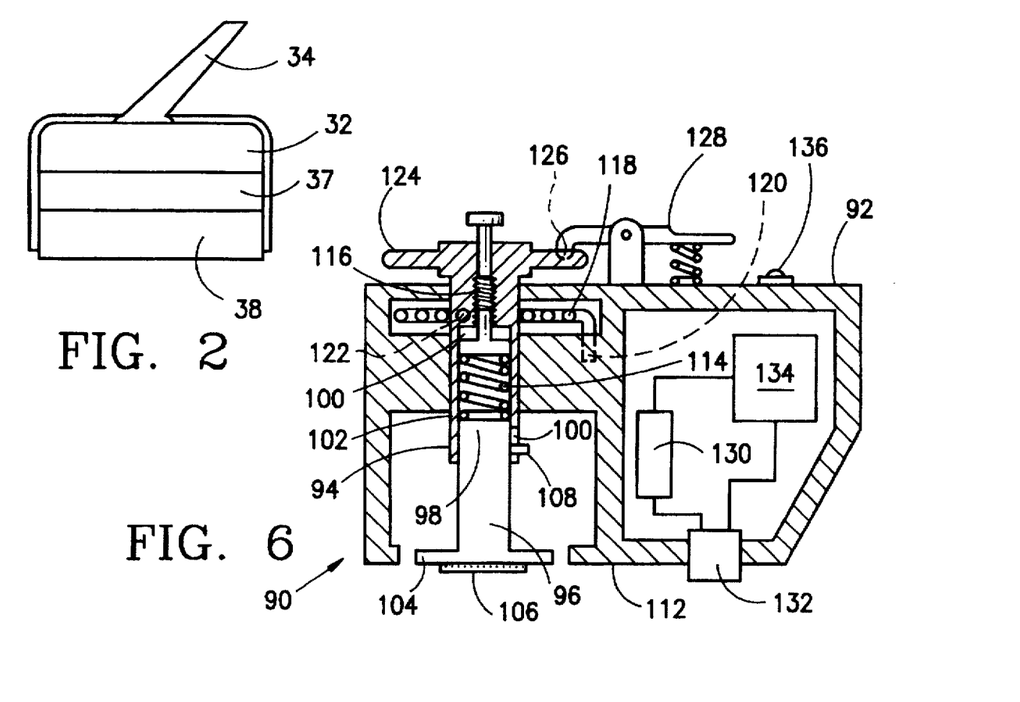
FIG. 2 is a sectional diagram of an electrode for the apparatus of FIG. 1.
FIG. 6 is a sectional view of a mechanical skin removal unit of the present invention.

For breast cancer screening, the electrodes 24 of the electrical array 22 should be mounted in a manner which permits the electrodes to be accurately positioned against the curved surface of the breast 16 while still maintaining uniform spacing and the position of the electrodes in a predetermined pattern. The electrode array 22 is used in conjunction with a reference electrode 30, and all of these electrodes are of a type suitable for detecting the potential level of the electromagnetic field present in a living organism. Ideally, the electrodes 24 and 30 should be of a type which do not cause a substantial battery effect between the organism under test and the electrode. An electrode for use as the electrodes 24 and 30 includes a layer of silver 32 having an electrical lead 34 secured in electrical contact therewith. In contact with the silver layer is a layer of silver chloride 37, and extending in contact with the silver chloride layer is a layer of ion conductive electrolyte gel material 38 which contacts the surface of a living organism. This gel can be in substantially a liquid gel or cream form or can be impregnated in a sponge foam holder, and gels with a high electrolyte concentration are preferable.

The device 10 is a multi-channel device having electrical electrode leads 34 extending separately from the electrodes 24 and the reference electrode 30 to a low pass filter 36. This filter operates to remove undesirable high frequency AC components which appear on the slowly varying DC voltage signal outputs provided by each of the electrodes as a result of the electromagnetic field measurement. The low pass filter 36 may constitute one or more multiple input low pass filters of known type which separately filter the signals on each of the input leads 34 and then pass each of these filtered signals in a separate channel to a multiple input analog-to-digital converter 40. Obviously, the low pass filter 36 could constitute an individual low pass filter for each of the specific channels represented by the leads 34 which would provide a filtering action for only that channel, and then each filtered output signal would be connected to the input of the analog-to-digital converter 40.

The converter 40 is a multiple input multiplex analog-to-digital converter of a known type, such as that manufactured by National Semiconductor, Inc. and designated as ADC808. For multiple channels, it is possible that more than one multiple input analog-to-digital converter will be used as the converter 40. For example, if an 8-input analog-to-digital converter is used and there are 24 input and output channels from the low pass filter 36, then the analog-to-digital converter 40 might include three 8-input converters.

The analog-to-digital converter 40 converts the analog signal in each input channel to a digital signal which is provided on a separate output channel to the multiple inputs of a central processing unit 42. The central processing unit is a component of a central control unit indicated generally at 44 which includes RAM and ROM memories 46 and 48. Digital input data from the analog-to-digital converter 40 is stored in memory and is processed by the CPU in accordance with a stored program to perform the diagnostic and scanning methods of the present invention.

The measurement data processed by the CPU 42 contains indications of the presence or absence of a disease or other body condition, such as a tumor, but those indications are not readily discernable from a casual inspection of the data. Instead, analysis of the data is required, and it is imperative that this analysis yield results that are consistent and reliable. collected data tends to be obscured by noise due to factors such as the low DC potentials involved and the innate complexity of biological systems. Biological systems are notorious for their complexity, and wide variances from the norm are not uncommon.

In order to accurately analyze the collected data in spite of the noise problem and the inherent nonlinearity of biopotential data, the present invention involves the use of a neural network to examine the data developed by the CPU 42 and identify patterns indicative of the presence or absence of a disease or other condition. Essentially, the neural network is a processing system wherein a simulated set of connected processing elements (neurons) react to a set of weighted input stimuli. The output from these neurons bears a nonlinear relationship to the input signal vector, with the nature of the relationship being determined by the strength of the connections. The connection strengths between the neurons must be set to values appropriate to the problem solution, and this is done in an indirect fashion by having the network "earn" to recognize information patterns. Once this is accomplished, the network can be called upon to identify a pattern from a distorted facsimile of the same pattern.

For use with the present invention, it is desirable to employ a neural network having a learning capability which is separate from the normal network function for data analysis. This is desirable because otherwise the network would continue to learn and evolve as it is used, making validation of the results impossible. Known networks of this type are commercially available, such as a product identified as Neuro Shell II (Backpropagation) from the Ward Systems Group, Inc.

The network is first trained to recognize disease or other condition or injury patterns using data resulting from known studies. Subsequently during use, similar data derived by the CPU as a result of processing is then fed to the neural network 49, and the output of the neural network is directed to an indicator device 50 which may constitute a printer, a CRT display device, or a combination of such indicators. The indicator device 50 may incorporate computer technology and graphics capable of imaging, in at least two dimensions, the disease or injury condition indicated by the output from the neural network.

In some instances, the separate analog to digital converter 40 can be eliminated and the central processing unit 42 can be formed from a microprocessor which directly receives the filtered analog signals and converts them to digital form. Also, although the neural network 49 is shown as a separate block for illustrative purposes in FIG. 1, it may in fact constitute a function performed by software for the central processing unit 42.

The operation of the discriminant analysis device 10 will be clearly understood from a brief consideration of the method steps of the invention which the device is intended to perform. When the lesion 14 or other condition has not been identified and a screening operation is performed to determine whether or not a lesion or other condition is present, a screening electrode array 22 is positioned in place on the site being screened with the electrodes 24 positioned over various diverse areas of the site. If a breast 16 is screened, the electrode array will cover either the complete breast or a substantial area thereof. The reference electrode 30 is then brought into contact with the skin of the subject 12 in spaced relationship to the electrode array 22, and this reference electrode might, for example, be brought into contact with a hand of the subject. Then, the electromagnetic field between the reference electrode and each of the electrodes 24 is measured, converted to a digital signal and stored for processing by the central processing unit 42. The program control for the central processing unit causes a plurality of these measurements to be taken over a period of time, and the measurements on all channels may be taken simultaneously and repetitively for the predetermined measurement time period. Alternatively, sequential measurements between the reference electrode and one of the electrodes 24 can be taken until each channel is sampled, and then the sequential measurement is repeated for the predetermined measurement period. In prior art units, a plurality of measurements have been taken over a period of time and often from a plurality of electrodes, but then these plural measurements are merely averaged to provide a single average output indication. In accordance with the method of the present invention, the measurement indications on each individual channel are not averaged with those from other channels, but are instead kept separate and averaged by channel within the central processing unit 42 at the end of the measurement period. For the duration of a single predetermined measurement period, for example, from sixteen measurement channels, the central processor will obtain sixteen average signals indicative of the average electromagnetic field for the period between the reference electrode 30 and each of the electrodes in the electrode array 22. Of course, more reference electrodes can be used, although only one reference electrode 30 has been shown for purposes of illustration.

Having once obtained an average signal level indication for each channel, the results of the measurements taken at multiple sites are analyzed in terms of a mathematical analysis to determine the relationships between the average signal values obtained. It has been found that the result of such an analysis is that a subset of relationships can be obtained which are indicative of the presence of a disease, injury or other body condition while a different subset might be obtained which will be indicative of the absence of these factors. Although either a discriminant mathematical analysis procedure on decision making logic may be designed to separately obtain and analyze the relationship between the average potential values in accordance with this invention for screening or diagnostic purposes, the discriminant mathematical analysis procedure to be hereinafter described in combination with data pattern recognition is a method which appears to be effective.

An important relationship to be obtained is designated the maximum voltage differential (MVD), which is defined as the minimum average voltage value obtained during the measurement period subtracted from the maximum average voltage value obtained for the same period where two or more electrodes are recording voltages from a test area. Thus, for each predetermined measurement period, the lowest average voltage level indication obtained on any of the channels is subtracted from the highest average voltage level indication obtained on any of the channels to obtain an MVD voltage level. If this MVD voltage level is above a desired level >x, then a disease, injury or other condition, such as a malignancy, could be indicated. Similarly, if the average taken over the measurement period from one channel is an abnormally low value <y, the presence of this abnormally low individual electrode reading (IER) could be indicative of a disease, injury or other condition. These primary indicators may be further analyzed in accordance with a neural network control program to be subsequently described to reduce the number of false positive diagnosis, usually cases of non-malignant hyperplasia which may be falsely identified as cancer on the basis of high MVD or low IER readings.

When the device 10 is used in accordance with the method of the present invention for a screening function where a specific lesion 14 has not yet been identified, using as an example breast screening where the patient is asymptomatic, an array 22 is employed which will give maximum coverage of the entire breast surface. Then the MVD level, and possibly an IER level is obtained in accordance with the method previously described as well as the average values for each channel. All of this data, namely, the average values, and the MVD level is input to the neural network 49 which has been trained to discern a pattern from the data which is indicative of a disease condition. This same process can be performed with electrodes of other types and electrodes other than surface electrodes, needle electrodes for invasive measurement, and electrodes which measure resistance or impedance can also be used.

Figure 3:
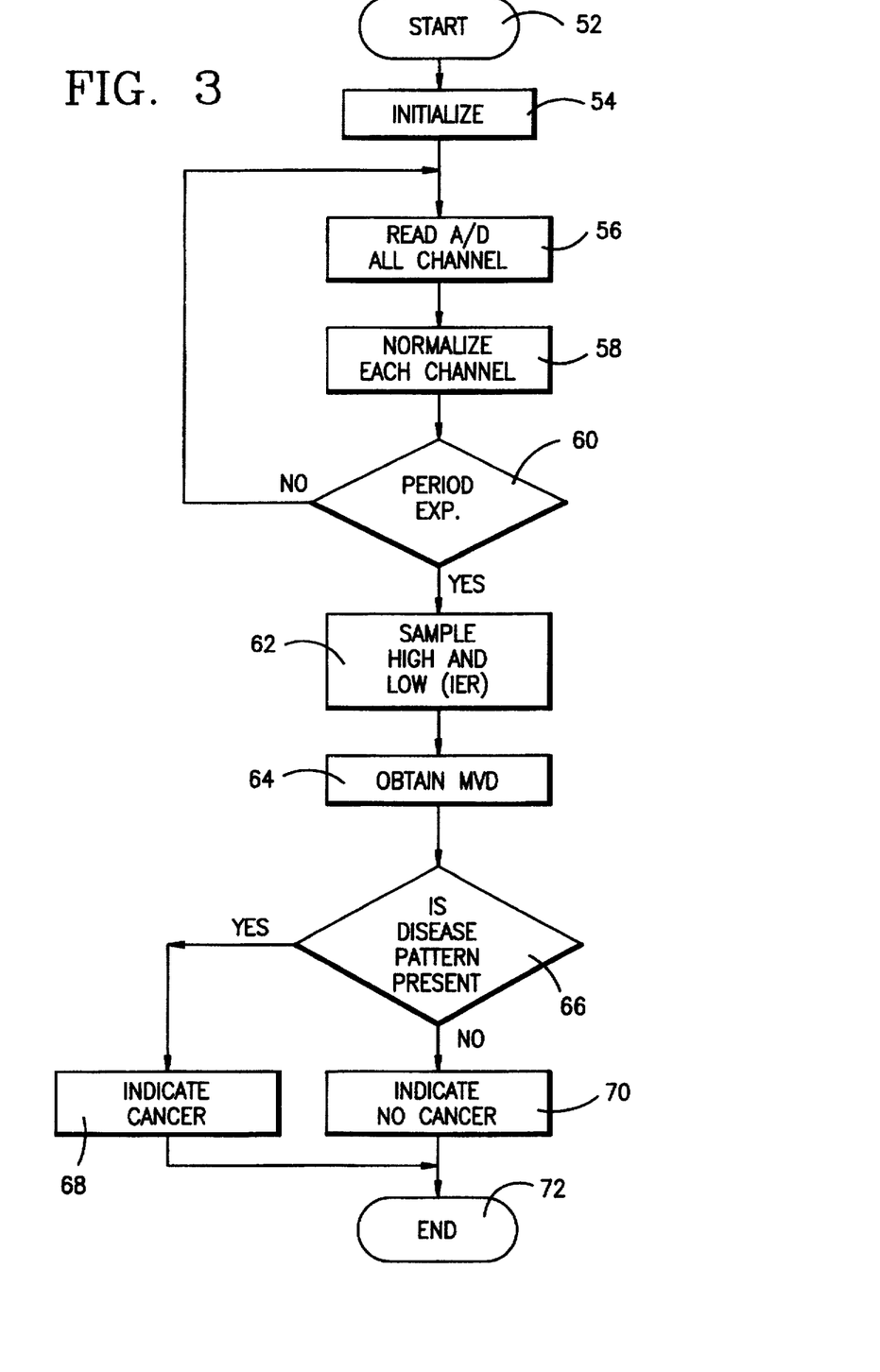
FIG. 3 is a flow diagram of the measurement operation of the apparatus of FIG. 1.

The general overall operation of the central processing unit 42 will best be understood with reference to the flow diagram of FIG. 3. The operation of the unit 10 is started by a suitable start switch as indicated at 52 to energize the central processing unit 42, and this triggers an initiate state 54. In the initiate state, the various components of the device 10 are automatically brought to an operating mode, with for example, the indicator 50 being activated while various control registers for the central processing unit are reset to a desired state. Subsequently, at 56, a predetermined multiple measurement period is initiated and the digital outputs which are either generated in the processing unit 42 or those from the analog-to-digital converter 40 are read. When an analog neural network 49 is employed, the analog values will be read at 56. The central processing unit may be programmed to simultaneously read all channel outputs or these channel outputs may be sequentially read.

Once the analog or digital signals from all channels are read, an average signal for each channel is obtained at 58 for that portion of the measurement period which has expired. The average or normalized value for each channel is obtained by summing the values obtained for that channel during the measurement period and dividing the sum by the number of measurements taken. Then, at 60, the central processing unit determines whether the measurement period has expired and the desired number of measurements have been taken, and if not, the collection of measurement samples or values continues.

Once the measurement period has expired, the microprocessor will have obtained a final average value for each channel derived from the measurements taken during the span of the measurement period. From these average values, the highest and lowest average values obtained during the measurement period are sampled at 62, and at 64, and the lowest average channel value which was sampled at 62 is subtracted from the highest average channel value to obtain a maximum voltage differential value. Then both the channel average values from 62 as well as the maximum voltage differential value from 64 are directed as inputs to the neural network at 66 which has been trained to recognize disease patterns from such data. Alternatively, only the maximum voltage differential values from 64 are directed to the neural network 66.

In the neural network at 66, if a disease or other condition pattern is identified from the input MVD signal values or the MVD signal values and the average signal values, then a probable disease indication, such as cancer present, is provided at 68, but if a disease pattern is not recognized, then the lack of a probable disease condition is indicated at 70. Since neural networks generally provide a probability statement, the probability of the presence or absence of a disease condition is indicated at 68 and 70, and the device may be used to distinguish high risk patients from low risk patients. After the indication of the probable presence or non-presence of a disease at 68 or 70, the routine is ended at 72.

The neural network 66 may be used to recognize other patterns derived from the DC biopotential signals provided by the device 10. For example, there is a phasicity pattern which occurs in the averaged electrical biopotentials over time which can be sensed, and variations in this phasicity pattern may be recognized as indicative of particular disease, injury or other conditions. Another pattern can be recognized in the phasicity of the multiplicity of individual electropotential values which are obtained by the device 10 prior to averaging. During a test period, individual measurements in the hundreds will be taken from each electrode for averaging, and phasicity changes in these individual values provide a complex pattern which can be analyzed by the neural network. Changes in this complex phasicity pattern can be identified as indicative of certain disease, injury or other conditions. It is contemplated that a combined analysis may be made using the phasicity pattern of the biopotential signals before averaging and a subsequent analysis of the phasicity pattern of the averaged signal values after averaging to obtain a combined analysis as an indicator of the presence or absence of a specific condition.

Figure 4:
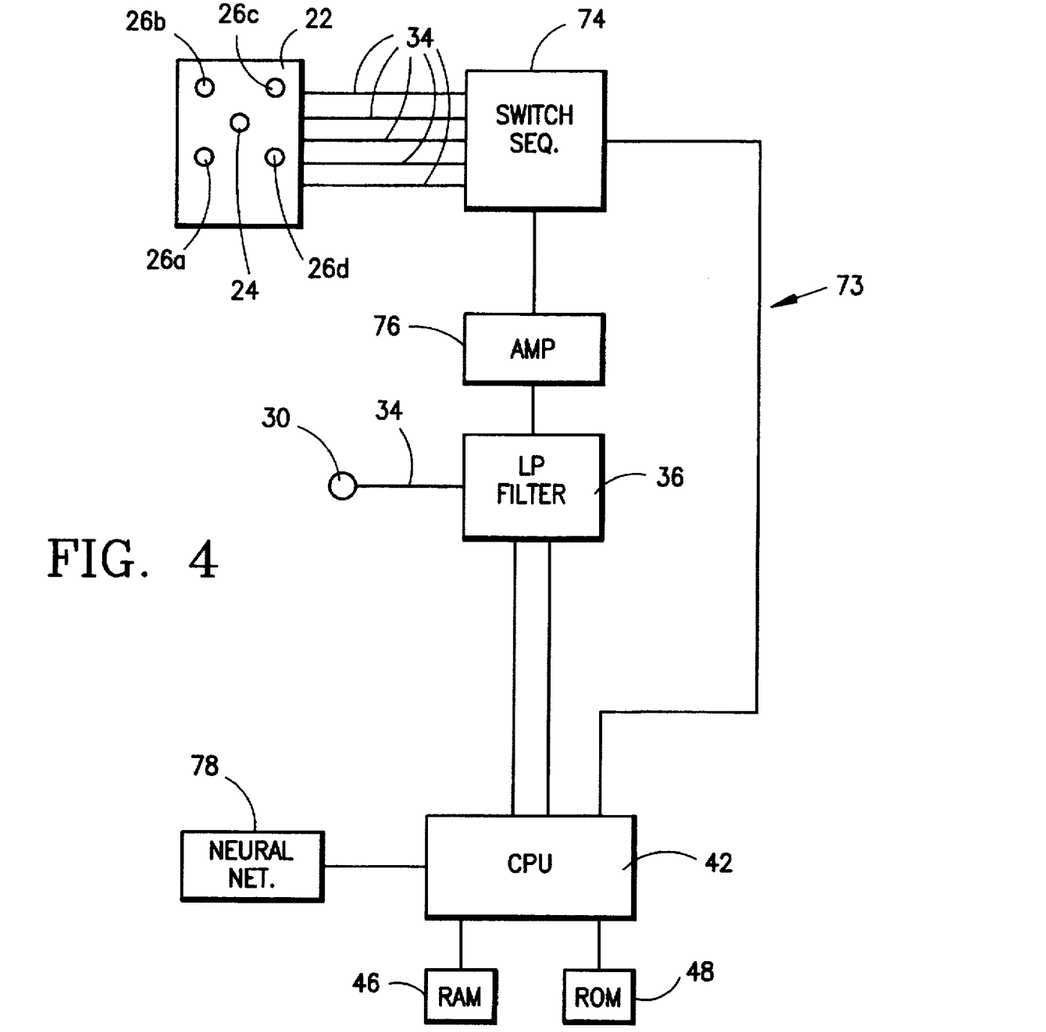
FIG. 4 is a block diagram of a second embodiment of the apparatus of the present invention.

The device of the present invention may be constructed to sequentially sample the output from each electrode 24 and 26 and provide sampled potentials over a single one amplifier channel. A sequential system of this type is shown in FIG. 4 at 73 where the outputs from the electrodes 24 and 26 are fed to a switching sequencer 74 which operates under the control of the central processor 42. The central processor causes the switching sequencer to sequentially provide the outputs from specific electrodes in sequence to an amplifier 76 and the low pass filter 36. Thus, a single amplifier and a single channel to the filter 36 handle all of the outputs from the electrode array 22.

When the switching sequencer 74 is provided under the control of the central processor 42, the reference electrode 30 may well be eliminated and an electrode in the electrode array 22 may function as the reference electrode. This is often advantageous, as it will place the reference electrode closer to the disease site and will substantially reduce or eliminate the effects of long term drift which occur when the reference electrode is remote from the disease site. Also, this provides great flexibility in measurement technique. For example, a single electrode in the array 22 can be chosen as the reference electrode for all measurements taken during a measurement period. On the other hand, the sequencer could different reference electrodes during the measurement period to provide measurements from different test and reference electrode combinations. In a sequential measurement operation, the sequencer could choose the electrode 26a of FIG. 4 as a reference electrode for taking a measurement with the electrode 26b as the test electrode, and then the electrode 26b could be sequenced to become the reference electrode while a measurement is taken with the electrode 26c. This sequence can continue using all electrodes or selected electrodes in the matrix during the test period.

Both the apparatus for condition screening or sensing 10 of FIG. 1 and the apparatus 73 of FIG. 4 may be either digital or analog units. For an analog unit, the analog to digital converter 40 is eliminated and the output of the low pass filter 36 is sent directly to the CPU 42 where the analog signals are averaged and an analog MVD signal is developed. These analog average and MVD signals are then provided as inputs to an analog neural network 78 which replaces the digital network 49 of FIG. 1. This circuit is shown in combination with the apparatus 73 of FIG. 4, but may be used equally well with the multichannel unit 10 of FIG. 1.

The apparatus for condition screening or sensing of the present invention may be used in a method for monitoring the efficacy of therapy for some diseases or injury conditions. A problem which arises in cancer treatment, for example, is assessing the efficacy of the treatment, whether it be by radiation or chemotherapy. However, since the electrical biopotential differentials obtained with the apparatus of the present invention provide an index of the relative levels of cell proliferation, they may be used to monitor the progress of various disease treatments. It has been found that the electrical potential differentials resulting from some cancers tend to change in response to chemotherapy. Thus once a cancer has been identified and an initial MVD level for that particular cancer has been computed, subsequent MVD levels are taken as treatment progresses and compared to previous MVD levels to determine whether or not a change is occurring. Depending upon the treatment in progress, a change, or in some instances a lack of change in the MVD level will tend to indicate that a therapy treatment is positive and is having some success.

Other conditions of the human body may also be effectively monitored using the method and apparatus of the present invention. For example, in females during ovulation, tissue rupture occurring incident to passage of the ova to the fallopian tubes results in significantly altered biopotential levels which can be sensed by the units of FIGS. 1 and 4. Symptoms caused by ovulation can be confused with those associated with appendicitis, but the high MVD levels resulting from ovulation can be used to differentiate between the two.

The efficacy of a variety of therapeutic treatments, such as post menopause hormone therapy and various immunal therapies may also be monitored using the method and apparatus of the present invention.

The use of the device and method of the present invention to provide an objective test for ovulation will be extremely useful in the prevention of an unwanted pregnancy as well as an aid in assisting women who are experiencing difficulties with infertility.

Another normal bodily function associated with pain is labor or uterine contractions related to the birth of a child. The measurement of DC biopotentials in accordance with the present invention during the occurrence of these conditions can be used to determine the effectiveness of the contractions in leading to cervical dilation and the probability of a normal vaginal delivery. Also, DC electrical biopotential measurements can be useful in distinguishing normal from abnormal delivery patterns as well as in the detection of fetal distress and abnormalities of labor such as separation of the placenta prematurely or infraction of the placenta.

In taking DC biopotential measurements, the interface between the measurement and reference electrodes and the skin of a subject is a source of high impedance and electronic noise which can cause high and unpredictable variations in the DC signal values measured. Therefore, it is important to minimize the noise and reduce the impedance resulting from this interface. It has been found that the presence of a relatively thick cornified epithelial layer of skin under an electrode contributes to high noise and impedance values at the interface, and care must be taken to remove this layer of skin or to position the electrode in another area. For example, a reference electrode or electrodes should be positioned on low impedance areas of the body such as the low-suprasternal notch or the skin over the xyphoid process or the subxyphoid area.

Selective positioning of the measurement electrodes is more difficult, as for effective screening, it is often necessary to space these electrodes substantially equal distances apart. Consequently, removal of some of the cornified epithelid layer must be accomplished in areas where electrodes are to be positioned. To accomplish this with electrocardiograph electrodes, a small patch of fine sandpaper has been developed which sticks to the finger of a technician and which can manually be manipulated to remove a skin layer. This manual technique is not acceptable for many DC biopotential measurement processes, as for example in breast screening for cancer, where the potential for injury to sensitive skin is high.

Figure 5:
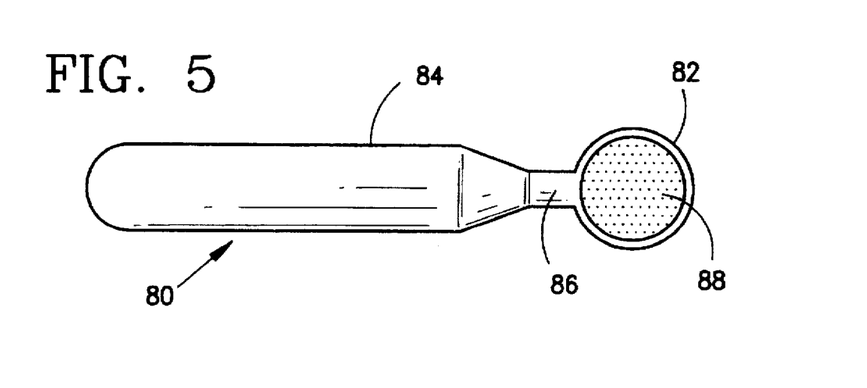
FIG. 5 is a plan view of a disposable skin removal unit of the present invention.

With reference to FIG. 5, a simple, throw away, skin removal device 80 is illustrated which operates effectively to remove dead surface skin without having the ability to apply a pressure sufficient to cause injury to other skin layers. This skin removal unit includes a head section 82 and a body section 84 of wood, plastic or similar substantially rigid material with the head section being joined to the body section by a neck section 86. A very fine abrasive layer 88 is applied to one surface of the head section and is adapted to be rubbed against the skin of a subject by manual reciprocatory movement of the body section when it is held in the hand of a technician. The neck section is designed to break or collapse if pressure on the abrasive layer and head section exceeds a pressure which is safe for the skin surface being abraded. This can be accomplished by reducing the cross sectional area of the neck section relative to that of the head and body sections or by forming the neck section of a flexible or spring material which flexes upwardly when too much pressure is applied to the head section.

Alternatively, skin layer removal can be mechanically accomplished with the adjustable skin removal unit 90 of FIG. 6. This unit includes a housing 92 to rotatably mount a spring biased assembly 94 that includes a shaft 96 having an upper end 98 which is received in the open end of a chamber 100 formed in a second shaft 102. An abrasive disc support 104 is formed at the lower end of the shaft 96 to receive a disposable disc of abrasive material 106. This disc is removably secured to the disc support by any suitable means, such as a pressure sensitive adhesive which permits the disc to be removed and discarded after use. A pin 108 projecting from the shaft 96 projects into and engages the lower end of a slot 110 formed in the shaft 102. This positions the shaft 96 relative to the housing 92 so that the abrasive disc 106 extends beneath a lower support surface 112 of the housing.

The shaft 96 is permitted to move longitudinally upward relative to the shaft 102 for a limited instance determined by the slot 110, and when the pin 108 reaches the uppermost limit of the slot, the abrasive disc 106 will have been moved inwardly of the housing 92 above the lower support surface 112 thereof. A spring 114 mounted within the chamber 100 engages the upper end 98 of the shaft 96 and biases the shaft so as to tend to maintain the pin 108 in contact with the lower extremity of the slot 110. The bias of this spring will determine the pressure which the abrasive disc 106 will apply to the skin of a patient, and when a preset pressure is exceeded, the shaft 96 will move upwardly against the bias of the spring 114 to reduce the pressure of the disc against the skin.

The bias of the spring 114 may be varied by rotating a threaded shaft 116 which extends through the upper end of the shaft 102 into contact with the upper end of the spring 114. The rotation of the shaft 102 is biased by a spring 118 having one end 120 connected to the housing 92 and a second end 122 connected to the shaft 102. The shaft 102 may be rotated against the bias of the spring 118 by a handle 124 positioned externally of the housing 92 and connected to the uppermost end of the shaft 102. When the shaft 102 is rotated to increase the bias of the spring 118, a detent 126 in the handle 124 engages the end of a pivoted, spring biased trigger 128. When the trigger 128 is pivoted out of the detent 124, the spring 118 rapidly rotates the shaft 102 which in turn rotates the shaft 96 through engagement with the pin 108. This caused the disc 106 to rotate against the skin of a subject.

The housing 92 may also contain an impedance measuring unit which measures the electrode interface impedance in the area where a portion of the skin layer has been removed by the disc 106 prior to the placement of an electrode 24, 26 or 30. This impedance measuring unit includes a DC power supply 130 connected to an electrode assembly 132 and an impedance measuring circuit 134. When the impedance at the interface between the electrode assembly 132 and the skin of a subject is within a low range sufficient for good operation of the electrodes in the electrode assembly 22, the impedance measuring circuit will permit current to flow to light an indicator light 136 which may be formed by an LED.

In accordance with the present invention, the mechanical skin preparation accomplished with devices such as those shown in FIGS. 5 and 6 prior to the application of electrodes may be replaced by chemical skin preparation. Keratolytic agents such as salicylic acid, glycolytic acid and acetic acid cause a swelling and disruption of the cornified epithelium, which results in a reduction of the impedance in a treated area at the electrode-skin interface. For example, tests have shown that the direct application of a 2% solution of salicylic acid in an over the counter Salicyclic Acid Acne Preparation on Double Textured Pads distributed by Proctor & Gamble under the trademark Clearasil® to the female breast causes about a two-fold reduction in skin impedance. To automatically achieve an impedance reduction at the skin-electrode interface, a keratolytic agent, such as salicylic acid, is added to the gel 38 in the electrode of FIG. 2 which forms the electrodes 24, 26 and 30 of FIG. 1. It has been found that a keratolytic agent, such as salicylic acid, may be dissolved in the gel without adversely affecting the electrolytic action of the gel. When the electrode is mounted on a subject with the gel in contact with the skin, the keratolytic agent in the gel causes a disruption of the cornified epithelium with a resultant reduction of impedance at the electrode-skin interface. The keratolytic agent should be within the range of 1–10% of the gel-agent mixture.

We claim:

1. An apparatus for determining the presence or absence of a condition at a test site on a human or animal subject by measuring DC electrical biopotentials at said test site comprising:

an electrode sensing assembly to detect DC biopotentials and provide output test potentials indicative thereof, said electrode sensing assembly including at least two DC biopotential sensing electrode pairs adapted for contact with the subject to detect DC biopotentials present in the area of said test site and to provide test potentials as a function of said detected biopotentials, and processing means connected to receive said test potentials provided by said sensing electrode pairs, and including neural network means programmed to detect a pattern of potentials indicative of the presence of said condition, said processing means operating to receive and process said test potentials to determine the presence or absence of said condition by operating to receive a plurality of test potentials from said sensing electrode pairs and to average said test potentials to obtain a plurality of average potentials, said processing means operating to provide said plurality of averaged potentials to said neural network means.

2. The apparatus of claim 1 wherein said processing means operates to compare said plurality of averaged potentials to obtain a maximum and minimum average potential therefrom, said processing means subsequently operating to obtain a differential value signal indicative of a difference between said maximum and minimum average potentials and to provide said differential value signal to said neural network means.

3. A method for determining the presence or absence of a condition at a test site on a human or animal subject as a function of an electromagnetic field present in the subject, said method comprising:

detecting respective biopotentials indicative of the electromagnetic field present in said subject at each of a plurality of measurement locations located in an area of the test site and at least one reference location on the subject;

comparing the respective biopotentials so obtained to identify a high and low level biopotential value;

obtaining a differential value indicative of the difference between said high and low level biopotential values;

and providing said differential value to a neural network programmed with similarly obtained differential values from reference subjects with said condition to detect potential patterns indicative of the presence of said condition.

4. The method of claim 3 which includes taking a plurality of biopotential measurements at each said measurement location during a measurement period, obtaining an average measurement value for each said measurement location from the biopotential measurements taken from said locations during the measurement period;

and comparing said average measurement values to identify therefrom said high and low level biopotential values.

5. The method of claim 4 which includes providing said average measurement values as inputs to said neural network.

6. The method of claim 4 wherein said low level biopotential value is the lowest average measurement value and said high level biopotential value is the highest average measurement value.

7. The method of claim 3 wherein the condition is labor.

8. The method of claim 3 wherein the condition is ovulation.

9. A method employing a neural network for determining the presence or absence of a condition at a test site on a human or animal subject as a function of DC biopotential values indicative of the electromagnetic field present in the subject, said method comprising:

programming said neural network to detect biopotential patterns indicative of said condition;

taking a plurality of DC biopotential measurements at each of a plurality of measurement locations located in an area of the test site during a measurement period to obtain a plurality of biopotential measurement values for each such location;

obtaining an average measurement value for each said measurement location from the biopotential measurements taken at such measurement location during said measurement period;

and providing said average measurement values as inputs to said neural network.

10. The method of claim 9 which includes programming said neural network to detect patterns of average measurement values and differential values derived from said average measurement values which are indicative of a condition, said method including comparing the average measurement values from a measurement period to identify a high and a low average measurement value, obtaining a differential value indicative of the difference between said high and low average measurement values, and providing said differential value as an input to said neural network.

11. An apparatus for determining the probability of the presence of a condition at a potential disease site on a human or animal subject by measuring the DC biopotentials which are indicative of the electromagnetic field present at the skin surface of the subject in an area of said potential disease site comprising:

reference electrode means for contacting the skin surface of the subject at a reference location, a plurality of test electrode means for contacting the skin surface of the subject at spaced locations in the area of the potential disease site, each said test electrode means operating with said reference electrode means to define a test-reference sensing means combination for detecting DC biopotentials indicative of the electromagnetic field present between said reference electrode means and said test electrode means during a test period and to provide a test signal as a function thereof;

processing means which operates to sample and receive a plurality of test signals from each test-reference sensing means combination during said test period and to average the test signals for said test period from each said test-reference sensing means combination to obtain an average signal value for each test-reference sensing means combination, said processing means including neural network means programmed with similarly obtained average signal values for reference subjects with said condition to detect a pattern of potential values indicative of the presence of said condition, said neural network means operating to receive said average signal values.

12. A method for determining the probability of the presence of breast cancer in a breast of a human test subject which includes obtaining a multiplicity of differential data values from a plurality of human reference subjects with breast cancer in a cancerous breast by detecting D.C. biopotentials at a plurality of spaced measurement locations on the cancerous breast, comparing the DC biopotentials so obtained for each human reference subject to obtain one or more differential values for each human reference subject indicative of differences between DC biopotentials obtained for such human reference subject, storing the differential values from the plurality of human reference subjects as differential data values, accessing the learning capability of a neural network having a supervised learning capability separate from a network application function for data analysis by providing said differential data values thereto, subsequently detecting a plurality of DC biopotentials at a plurality of spaced measurement locations on the breast of a test subject, comparing the DC biopotentials so obtained from the test subject to obtain one or more test differential values, and accessing the network application function for data analysis of said neural network by providing said test differential values thereto.

13. The method of claim 12 which includes obtaining said multiplicity of differential data values by contacting the skin surface of each human reference subject with at least one reference electrode at a reference location and the skin surface of the cancerous breast of said reference subject at spaced locations with a plurality of test electrodes, each said test electrode operating with a reference electrode to provide a test-reference electrode sensing combination for detecting DC biopotentials during a test period,     initiating a test period and obtaining a plurality of DC biopotentials with each said test-reference electrode combination during the test period,     at the end of the test period averaging the plurality of DC biopotentials obtained for each test-reference electrode combination to derive an average value for each test-reference electrode combination,     comparing the average values so obtained to determine the highest and the lowest average values, and     obtaining a differential value indicative of the difference between said highest and lowest average values as the differential value for a reference subject for a test period.

14. The method of claim 13 which includes obtaining the test differentials from a test subject by contacting the skin surface of a test subject with at least one reference electrode at a reference location and the skin surface of a breast of the test subject at spaced locations with a plurality of test electrodes, each said test electrode operating with a reference electrode to provide a test-reference electrode sensing combination for detecting DC biopotentials during a test period,     initiating a test period and obtaining a plurality of DC biopotentials with each said test-reference electrode combination during the test period,     at the end of the test period averaging the plurality of DC biopotentials obtained for each test-reference electrode combination to derive an average value for each test-reference electrode combination,     comparing the average values so obtained to determine the highest and the lowest average value, and     obtaining a differential value indicative of the difference between said highest and lowest average values as the differential value for said test subject.

15. An apparatus for determining the probability of the presence of a condition at a test site on a human subject by measuring DC electrical biopotentials at said test site comprising     at least one DC biopotential reference electrode for contacting the skin surface of the subject at a reference location,     a plurality of DC biopotential test electrodes for contacting the skin surface of the subject at spaced locations in the area of the test site, each said test electrode operating with a reference electrode to provide a test-reference sensing combination for detecting a DC biopotential during a test period and to provide a test signal as a function thereof;

processing means operative to receive a plurality of test signals from each said test-reference combination during a test period and to separately average the test signals for said test period from each said test-reference sensing combination to obtain a test average signal value for each test-reference sensing combination, said processing means operating to compare said test average signal values to obtain at least one test differential value indicative of a difference between said test average signal values,     and a neural network means previously programmed with reference differential values indicative of differences between reference average signal values similarly obtained by averaging test signals from each of a plurality of test-reference sensing combinations applied to reference subjects having said condition to recognize a condition pattern indicative of said condition, said neural network means operating to receive said test differential value from said processing means to provide an output indicating the probability of the presence of said condition.

16. The apparatus of claim 12 wherein said neural network means is also programmed with reference average signal values similarly obtained from test signals from a plurality of test-reference sensing combinations applied to reference subjects having said condition, said neural network means also operating to receive said test average signal values from said processing means.

* * * * *